US 7,118,533 B2

(12) United States Patent
Kime et al.

(10) Patent No.: US 7,118,533 B2
(45) Date of Patent: Oct. 10, 2006

(54) DISINFECTING AND STORAGE APPARATUS FOR A TRANS-ESOPHAGEAL PROBE

(76) Inventors: Mark Chandler Kime, 1500 Wood St., Valparaiso, IN (US) 46383; Richard Hartley Johnston, 11152 W. State Road 2, Westville, IN (US) 46391

( * ) Notice: Subject to any disclaimer, the term of this patent is extended or adjusted under 35 U.S.C. 154(b) by 253 days.

(21) Appl. No.: 10/249,762

(22) Filed: May 6, 2003

(65) Prior Publication Data
US 2003/0208115 A1    Nov. 6, 2003

Related U.S. Application Data

(60) Provisional application No. 60/377,732, filed on May 6, 2002.

(51) Int. Cl.
*A61B 8/00*    (2006.01)
(52) U.S. Cl. ...................... 600/462; 134/170
(58) Field of Classification Search ........... 600/437, 600/459–471, 121–125, 133, 198, 101; 134/21, 134/22.1–22.19, 25.1, 61, 84, 88, 91–92, 134/166 R, 170; 422/300
See application file for complete search history.

(56) References Cited

U.S. PATENT DOCUMENTS

| | | | | |
|---|---|---|---|---|
| 4,748,007 A | * | 5/1988 | Gaudion et al. ........... 422/300 |
| 5,090,433 A | * | 2/1992 | Kamaga ................... 134/169 C |
| D329,094 S | * | 9/1992 | Houman ................... D24/217 |
| 5,511,568 A | * | 4/1996 | Bowman et al. ......... 134/102.2 |
| D385,633 S | * | 10/1997 | De Rosa .................... D24/217 |
| 5,752,286 A | * | 5/1998 | Wright ..................... 15/104.92 |
| 6,132,691 A | * | 10/2000 | Coles ......................... 422/300 |
| 6,361,751 B1 | * | 3/2002 | Hight, III ................... 422/292 |

\* cited by examiner

*Primary Examiner*—Francis J. Jaworski
(74) *Attorney, Agent, or Firm*—Davis Wright Tremaine LLP

(57) ABSTRACT

An apparatus adapted for use with a trans-esophageal probe. The apparatus comprises a disinfecting unit and a storage unit, each of which includes a tubular housing having an interior, upper and lower ends, and an opening at the upper end for access to the interior. The disinfecting unit includes a support above the upper end of its housing for supporting a handle of a probe whose probe end is within the interior of the housing. The interior of the disinfecting unit is adapted to contain a fluid, and is equipped with a fluid level indicator and a drain for draining the fluid from the housing. The storage unit includes an enclosure removably mounted to the upper end of its housing for enclosing the handle end of a probe whose probe end is within the interior of the housing. Both units further include a support for a connector of a probe placed in the unit.

17 Claims, 1 Drawing Sheet

DISINFECTING AND STORAGE APPARATUS FOR A TRANS-ESOPHAGEAL PROBE

CROSS REFERENCE TO RELATED APPLICATIONS

This application claims the benefit of U.S. Provisional Application No. 60/377,732, filed May 6, 2002.

BACKGROUND OF INVENTION

1. Field of the Invention

The present invention generally relates to systems for disinfecting medical equipment. More particularly, this invention relates to units for disinfecting, drying and storing trans-esophageal probes.

2. Description of the Related Art

Trans-esophageal echocardiography (TEE) is generally a sonographic technique that involves the use of a probe to assess cardiac function, including valvular and left ventricular function both during and after heart surgery, congenital heart disease, arteriosclerosis and other conditions of the aorta, the detection of intracardiac defects, etc. The probe is equipped with an ultrasonic transducer mounted at its tip, which is placed in a patient's esophagus through the oral cavity. As such, TEE is a relatively fast and non-invasive procedure for monitoring the heart. TEE probes have some common features, such as the ultrasonic transducer mounted to a distal tip, a proximal handle equipped with controls (e.g., knobs) by which the tip can be manipulated, a connector for connecting the probe to an echocardiography unit, and a shaft (between the distal tip and handle) with a sufficient length to place the transducer at a location within the esophagus in proximity to the heart.

As with other reusable medical probes that are placed in a patent during use, it is essential that TEE probes be disinfected following the procedure. A current technique for disinfecting a TEE probe is to submerse the probe in a bath of a powerful disinfectant, such as gluteraldahyde. While effective, a significant drawback of this technique is the need to use an exhaust hood to limit the technician's exposure to the disinfectant, which is often contained in an oblong pan in order to permit the transducer and shaft of the probe to be simultaneously submerged. Risk of exposure to the disinfectant also occurs when filling and emptying the pan.

SUMMARY OF INVENTION

The present invention provides an apparatus adapted for use with a trans-esophageal probe having a handle end, an oppositely-disposed probe end, and a connector for connecting the probe to an echocardiography unit. The apparatus comprises at least one, and preferably both, of a disinfecting unit and a storage unit.

The disinfecting unit includes a substantially tubular housing having an interior for containing a fluid, an upper end, and an oppositely-disposed lower end, the upper end having an opening for access to the interior of the housing. Means is provided above the upper end of the housing for supporting the handle end of the probe while the probe end thereof is within the interior of the housing. The disinfecting unit further includes means for supporting the connector of the probe while the handle end of the probe is supported by the handle supporting means, means for indicating the level of fluid within the housing, and means for draining the fluid from the housing.

Similar to the disinfecting unit, the storage unit also comprises a substantially tubular housing having an interior, an upper end, and an oppositely-disposed lower end, with the upper end of the housing having an opening for access to its interior. The storage unit further includes means removably mounted to the upper end of its housing for enclosing the handle end of the probe while the probe end thereof is within the interior of the housing, and means for supporting the connector of the probe while the probe end is within the interior of the housing and the handle end is enclosed by the enclosing means.

A significant advantage of this invention is that a trans-esophageal probe can be disinfected with the disinfecting unit of this invention by filling the interior of the disinfecting unit housing with an appropriate disinfectant fluid, and then inserting the probe end of the probe into the interior of the housing such that the probe end and a substantial portion of the probe (a shaft between the probe and handle ends) is immersed in the disinfectant fluid. The probe can then be dried and stored by placing the probe end of the probe into the interior of the storage unit housing such that the probe end and a substantial portion of the probe (the shaft between the probe and handle ends) is within the interior of the housing, and then closing the upper end of the housing so as to minimize the release of vapors of the disinfectant fluid while the probe is allowed to dry.

Other objects and advantages of this invention will be better appreciated from the following detailed description.

DETAILED DESCRIPTION

Figure 1:
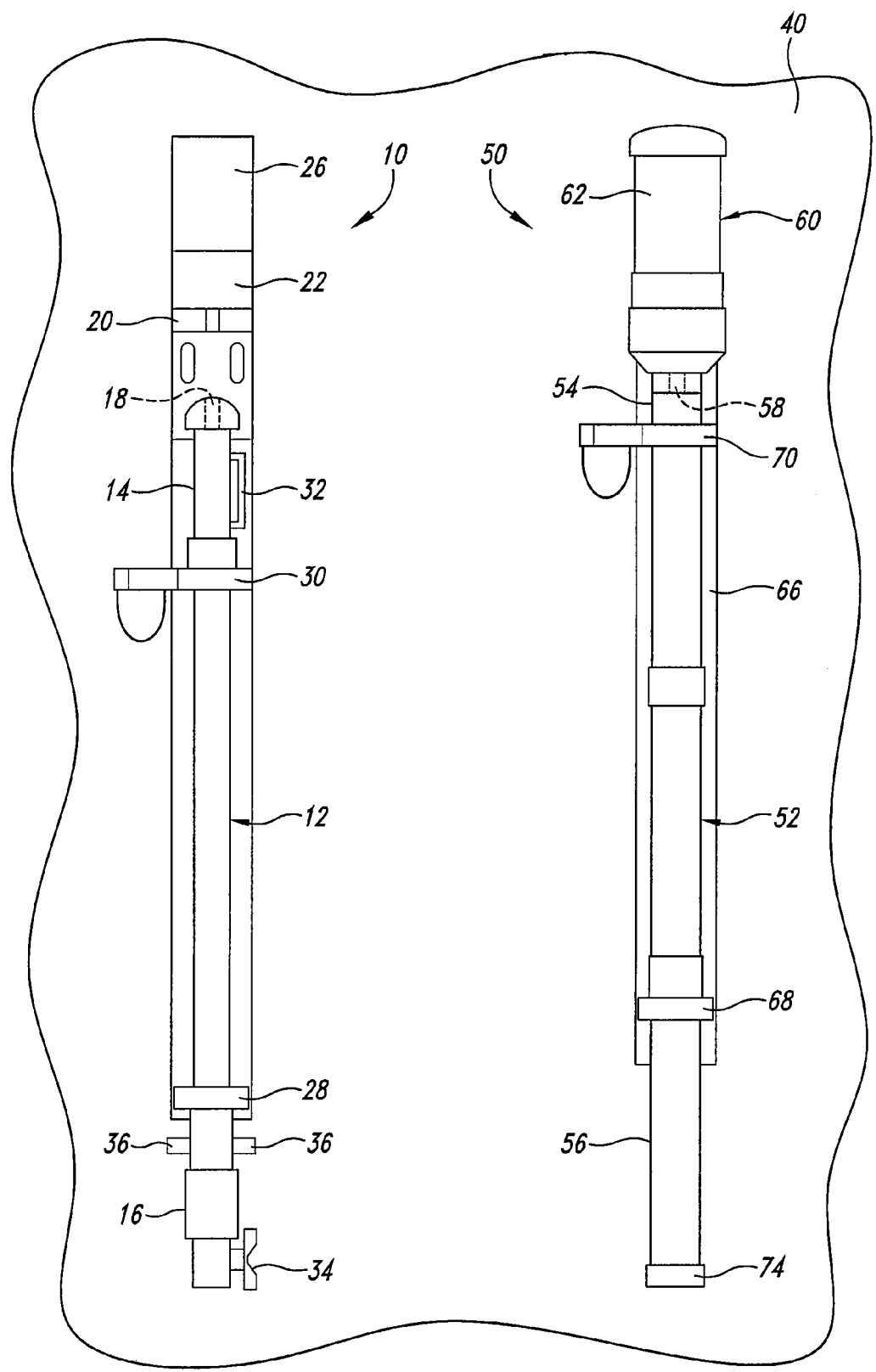
FIG. 1 is a frontal view of disinfecting and storage units for a trans-esophageal probe in accordance with preferred embodiments of this invention.

FIG. 1 represents components of a disinfecting and storage system for trans-esophageal probes (not shown) of a well-known type having a handle end, an oppositely-disposed probe end, and a connector for connecting the probe to a conventional echocardiography unit. The system comprises a disinfecting unit 10 and a storage unit 50 commonly mounted, such as to a wall 40 of an examination room. While the units 10 and 50 are intended to be used together, they may be used separately.

The disinfecting unit 10 is shown as comprising a substantially vertical, tubular-shaped housing 12 that defines an interior cavity for containing a disinfectant fluid, such as gluteraldahyde. The interior of the housing 12 is preferably capable of containing about 2.5 liters of disinfectant fluid, though lesser and greater capacities are foreseeable. The housing 12 has an upper end 14 and an oppositely-disposed lower end 16, with the upper end 14 having an opening 18 for access to the interior of the housing 12. The opening 18 is preferably sized so that the probe end of a trans-esophageal probe can be received therethrough, and so that the opening 18 is substantially closed by the shaft of the probe between its probe end and handle. The upper end 14 of the housing 12 is also adapted to permit disinfectant to be added to the unit 10 as needed. Notably, the surface area of a disinfectant within the housing 12 is far less than that exposed if the same amount of disinfectant was placed in a pan for disinfecting a probe in a conventional manner, such that exposure and evaporation of the disinfectant are drastically reduced.

The disinfecting unit 10 shown in FIG. 1 has a probe support 20 located above and spaced apart from the upper end 14 of the housing 12 for supporting the handle end of the probe while the probe end thereof is within the interior of the housing 12. The probe support 20 is shown as a horizontal slotted plate mounted to a vertical plate 22, with slots 24 machined in the plate 22 to enable the plate 22 to be adjustably mounted to a backing plate 26 with screws (not shown). The lower end 16 of the housing 12 is shown as being secured to the same backing plate 26 with a fitting 28. A connector support 30 mounted to the housing 12 is adapted for supporting the connector of the probe while the handle end of the probe is supported by the probe support 20. When mounted to the wall 40, the entire disinfecting unit 10 projects a minimal distance (e.g., several inches) from the wall 40.

A fluid level gage 32 is shown located between the connector support 30 and the upper end 14 of the housing 12. The gage 32 is a clear tube connected at its upper and lower ends to the interior of the housing 12, so that the level of disinfectant in the housing 12 can be determined. Finally, a drain 34 is provided at the lower end 16 of the housing 12 to allow the disinfectant fluid to be quickly drained from the interior of the housing 12 while the unit 10 remains mounted to the wall 40. FIG. 1 also depicts the housing 12 of the disinfecting unit 10 as being equipped with optional connectors 36, by which electrical leak testing can be performed.

In view of the above, the housing 12 of the disinfecting unit 10 is adapted to store a disinfectant over extended periods of time, so that the need to transfer a disinfectant to and from the housing 12 is minimized. Furthermore, a trans-esophageal probe can be disinfected with minimal exposure to the technician.

The storage unit 50 is shown in FIG. 1 as comprising a housing 52 that, similar to the housing 12 of the disinfecting unit 10, has a tubular shape and is intended to be mounted substantially vertical. The housing 52 has an interior cavity, an upper end 54, and an oppositely-disposed lower end 56, with the upper end 54 having an opening 58 for access to the interior of the housing 52. As with the disinfecting unit 10, the opening 58 in the housing 52 is also preferably sized so that the probe end of a trans-esophageal probe can be received therethrough, and so that the opening 58 is substantially closed by the shaft of the probe between its probe end and handle. A probe handle enclosure 60 is mounted to the upper end 54 of the housing 52, by which the handle end of the probe can be enclosed while the probe end thereof is within the interior of the housing 52. The handle enclosure 60 is shown as having a cylindrical shape, and preferably has a translucent or transparent wall 62 so that the handle of the probe can be seen when the probe is housed in the storage unit 50. The upper and lower ends 54 and 56 of the housing 52 are shown as being secured to a backing plate 66 with a fitting 68 and connector support 70. The construction and function of the connector support 70 are similar to the connector support 30 of the disinfecting unit 10, namely, to support the connector of a probe housed in the storage unit 50. Finally, a cap 74 closes the lower end 56 of the housing 52 so that, with the handle enclosure 60, the interior of the housing 52 is substantially vapor-tight. As such, vapors are not released to the environment while the probe is drying within the storage unit 50. The handle enclosure 60, connector support 70 and cap 74 preferably can be disassembled from the housing 52 to permit cleaning of the storage unit 50.

A suitable material for the housings 12 and 52 is polyvinyl chloride (PVC), though other materials could be used. Preferred materials for the supports 20, 30 and 70 and fittings 28 and 68 include ultrahigh molecular weight (UHMW) polyethylene, though other materials could again be used.

While the invention has been described in terms of a preferred embodiment, it is apparent that other forms could be adopted by one skilled in the art. For example, the physical configuration could differ from that shown, and materials and processes other than those noted could be used. Therefore, the scope of the invention is to be limited only by the following claims.

The invention claimed is:

1. An apparatus for a trans-esophageal probe having a handle end, an oppositely-disposed probe end, and a connector for connecting the probe to an echocardiography unit, the apparatus comprising a disinfecting unit and a storage unit;

wherein the disinfecting unit comprises:
  a substantially tubular first housing having an interior for containing a fluid, an upper end, and an oppositely-disposed lower end, the upper end having an opening for access to the interior of the first housing, the opening in the upper end and the probe end of the probe being sized so that the opening is substantially closed by the probe end when the probe end is received in the first housing;
  probe support means above the upper end of the first housing for supporting the handle end of the probe while the probe end thereof is within the interior of the first housing;
  first means for supporting the connector of the probe while the handle end of the probe is supported by the probe support means;
  means for indicating the level of fluid within the first housing; and
  means for draining the fluid from the first housing;
and wherein the storage unit comprises:
  a substantially tubular second housing having an interior, an upper end, and an oppositely-disposed lower end, the upper end of the second housing having an opening for access to the interior of the second housing;
  means removably mounted to the upper end of the second housing for enclosing the handle end of the probe while the probe end thereof is within the interior of the second housing; and
  second means for supporting the connector of the probe while the probe end is within the interior of the second housing and the handle end is enclosed by the enclosing means.

2. The apparatus according to claim 1, wherein the probe support means is adjustably mounted above the opening in the upper end of the first housing to enable the handle end of the probe to be supported above and spaced apart from the upper end of the first housing while the probe end of the probe is within the interior of the first housing.

3. The apparatus according to claim 1, wherein the draining means of the disinfecting unit is located at the lower end of the first housing.

4. The apparatus according to claim 1, wherein the lower end of the second housing of the storage unit is closed.

5. The apparatus according to claim 4, wherein the upper end of the second housing of the storage unit is closable with the enclosing means so that the interior of the second housing is substantially vapor-tight.

6. The apparatus according to claim 1, wherein the first connector supporting means is secured to the first housing of the disinfecting unit.

7. The apparatus according to claim 1, wherein the second connector supporting means is secured to the second housing of the storage unit.

8. The apparatus according to claim 1, further comprising means for mounting the disinfecting unit to a wall.

9. The apparatus according to claim 1, further comprising means for mounting the storage unit to a wall, the first housing and the probe support means being secured to the mounting means, the probe support means being adjustably secured to the mounting means to enable the handle end of the probe to be adjustably supported above the upper end of the first housing while the probe end of the probe is within the interior of the first housing.

10. An apparatus comprising:
  a trans-esophageal probe having a handle end, an oppositely-disposed probe end, and a connector for connecting the probe to an echocardiography unit;
  a disinfecting unit comprising:
    a first backing plate;
    a substantially vertical and tubular first housing secured to the first backing plate, the first housing having an interior for containing a disinfectant fluid, an upper end, and an oppositely-disposed lower end, the upper end having an opening for access to the interior of the first housing, the opening in the upper end and the probe end of the probe being sized so that the opening is substantially closed by the probe end when the probe end is received in the first housing;
    probe support means adjustably secured to the first backing plate so as to be above and spaced apart from the opening in the upper end of the first housing, the probe support means being adapted to support the handle end of the probe while the probe end thereof is within the interior of the first housing;
    first means for supporting the connector of the probe while the handle end of the probe is supported by the probe support means;
    means for indicating the level of the disinfectant fluid within the first housing; and
    a drain at the lower end of the first housing for draining the disinfectant fluid from the interior of the first housing;
  and a storage unit comprising:
    a second backing plate;
    a substantially vertical and tubular second housing secured to the second backing plate, the second housing having an interior, an upper end, and an oppositely-disposed closed lower end, the upper end of the second housing having an opening for access to the interior of the second housing, the opening in the upper end and the probe end of the probe being sized so that the opening is substantially closed by the probe end when the probe end is received in the second housing;
    means removably mounted to the upper end of the second housing for enclosing the handle end of the probe while the probe end thereof is within the interior of the second housing; and
    second means for supporting the connector of the probe while the handle end of the probe is enclosed by the enclosing means.

11. The apparatus according to claim 10, wherein the first connector supporting means and the fluid level indicating means are mounted to the first housing.

12. The apparatus according to claim 10, wherein the second connector supporting means and the enclosing means are mounted to the second housing.

13. The apparatus according to claim 12, wherein the
  second connector supporting means and the enclosing means can be disassembled from the second housing.

14. The apparatus according to claim 10, wherein the upper end of the second housing is closable with the enclosing means so that the interior of the second housing is substantially vapor-tight.

15. The apparatus according to claim 10, wherein the first backing plate is secured to a wall.

16. The apparatus according to claim 15, wherein the second backing plate is secured to the wall adjacent the first backing plate.

17. The apparatus according to claim 10, wherein the second backing plate is secured to a wall.

* * * * *